United States Patent [19]

Kleinke et al.

[11] Patent Number: 4,583,523
[45] Date of Patent: Apr. 22, 1986

[54] IMPLANTABLE HEART ASSIST DEVICE AND METHOD OF IMPLANTING SAME

[75] Inventors: Bernard L. Kleinke, San Diego, Calif.; Maynard L. Freeman, Lisle, Ill.

[73] Assignee: Lloyd & Associates, Lisle, Ill.

[21] Appl. No.: 627,113

[22] Filed: Jul. 2, 1984

[51] Int. Cl.⁴ .......................... A61F 1/24; A61H 31/00
[52] U.S. Cl. .................................................... 128/1 D
[58] Field of Search ............... 128/1 D, 60; 604/153; 417/412, 474, 478, 510

[56] References Cited

U.S. PATENT DOCUMENTS

| | | | |
|---|---|---|---|
| 3,048,121 | 8/1962 | Sheesley | 417/478 |
| 4,014,318 | 3/1977 | Dockum et al. | 417/412 |
| 4,143,425 | 3/1979 | Runge | 128/1 D |
| 4,176,411 | 12/1979 | Runge | 417/478 |
| 4,192,293 | 3/1980 | Asrican | 128/1 D |
| 4,195,623 | 4/1980 | Zeff et al. | 128/1 D |
| 4,293,961 | 10/1981 | Runge | 128/1 D |
| 4,304,225 | 12/1981 | Freeman | 128/60 |
| 4,384,829 | 5/1983 | Conley et al. | 128/1 D |
| 4,448,190 | 5/1984 | Freeman | 128/60 |
| 4,457,673 | 7/1984 | Conley et al. | 128/1 D |
| 4,488,099 | 12/1984 | La Forge et al. | 128/1 D |
| 4,506,658 | 3/1985 | Casile | 128/1 D |

Primary Examiner—William E. Kamm
Assistant Examiner—Mitchell J. Shein
Attorney, Agent, or Firm—Bernard L. Kleinke

[57] ABSTRACT

The implantable heart assist device includes an elongated assembly extending transversely between the ribs of a person from the rib cage to the aorta of the heart to be assisted. The elongated assembly includes an aorta compressing device at the front end thereof for engaging the aorta externally thereof. A mounting device at the rear end of the elongated assembly supports the device from the ribs of the person, and a motive device actuates and deactivates the compressing means alternatingly to help pump blood through the aorta.

To implant the heart assist device, a small incision is made at an area between the ribs, and the heart assist device is inserted through the incisional opening between the ribs. The mounting device is then affixed to the rib cage, and the motive device is then activated to cause the aorta compressing device to compress and release the aorta repeatedly.

16 Claims, 12 Drawing Figures

IMPLANTABLE HEART ASSIST DEVICE AND METHOD OF IMPLANTING SAME

DESCRIPTION

1. Technical Field

The present invention relates in general to a new and improved implantable heart assist device, and a method of implanting it. The invention relates more particularly, to an implantable left ventricular assist device, and a method of implanting it.

2. Background Art

There have been many different types and kinds of medical devices and surgical procedures adapted for treating heart disease. For example, mechanical pumps have been implanted surgically to replace the heart function in the circulatory system. The pump is typically actuated and controlled by an external, large base unit, having an air compressor. The air compressor is connected in fluid communication with the implanted pump by means of air lines connected through an opening in the chest wall of the patient.

Therefore, the activity of the patient is greatly restricted, since the patient must be tethered to the large, heavy life-supporting base unit at all times, in order to maintain the proper operation of the implanted pump. Moreover, there have been problems of rejection of the pump by the body. Also, since the blood comes into contact with the pump, the blood can become injured as a result of the pumping action. Moreover, the compressed air entering the chest cavity over a long period of time, for driving the heart pump, can be a vehicle for transmitting infection to the patient, even though elaborate filter systems are normally employed.

For short term use only, usually following surgery, intra-aortic balloon heart pumps have been employed. For example, reference may be made to U.S. Pat. No. 3,505,987. Such a device shown therein includes an inflatable balloon or the like device which is inserted into the aorta extending from the heart, and then alternatingly inflated and deflated in synchronization with the beating of the heart, for creating counter-pulsation to assist the heart function. In this regard, the balloon, when inflated, propels blood distally within the aorta to help improve the circulation of the patient. Moreover, blood is also forced within the aorta toward the heart, and thus into the coronary arteries to help nourish and strengthen the heart muscle.

However, the balloon comes into direct contact with the blood flowing in the aorta, and can cause adverse effects. Also, the balloon must be inflated by means of a tube which connects the balloon in fluid communication with the output of an air compressor.

Thus, while such an apparatus has been employed successfully for some applications, due to the adverse side effects and the tethering to the air compressor apparatus, it has not proven to be entirely acceptable for very long term use. Also, the opening in the body for admitting the air tube must be cleaned meticulously on a daily basis to avoid infection. Furthermore, the pumping of air into the body is not considered as being entirely safe condition, since leakage of air into the body from the unit would be highly undesirable and dangerous to the patient.

In an attempt to design a long term implantable heart assist device, and one which does not require air tubes, an experimental electrical device was developed and is disclosed in an article, entitled "The Experimental Use of the Diaphragm as an Auxiliary Myocardium", by Adrian Kantrowitz, et al, Surgical Forum, 1958, Volume IX, pages 266-268. The Kantrowitz experimental device was adapted to function with a portion of the human diaphragm (the left hemidiaphragm—a muscle normally used for contracting the lungs), which is removed surgically from the patient and then wrapped and sutured in place about the aorta. The diaphragm muscle is then stimulated electrically by two wires extending through an opening in the chest cavity from the diaphragm muscle to a source of electricity, to cause the diaphragm muscle to contract, and thus to achieve counter-pulsation, without any portion of the device coming into contact with the blood being pumped.

However, even though the experiment appeared successful, the Kantrowitz surgical procedure does not appear to be practical for long term use. In this regard, a portion (the diaphragm) of the body must be mutilated, and thus the breathing function would become severly impaired. Also, the early Kantrowitz technique does not appear feasible for long term use, since it is highly doubtful that the diaphragm muscle could be stimulated artificially in this manner, repeatedly, without destroying the muscle function, after months of use.

Thus, it would be highly desirable to have a totally implantable left ventricular assist device, whcih would not come into direct contact with the blood, and which could be used repeatedly for long term use. Such a device must be relatively simple in its operation so as to function properly for long periods of time to assit the heart function. A device meeting those specifications has been disclosed in U.S. Pat. No. 4,304,225. The device shown in that patent is mounted to a rib of the patient and includes a means for compressing a lower portion of the heart to facilitate the functioning thereof. Additionally, there is shown in co-pending patent application, Ser. No. 06/285,302, filed July 20, 1981, another device, which is mounted to the spine of the patient for compressing the aorta mechanically and repeatedly to achieve counter-pulsation.

While the foregoing mentioned two devices are advantageous for many applications, it would be highly desirable to have an improved heart assist device, which could be quickly and totally implantable in a relatively convenient manner, to minimize, or at least greatly reduce trauma to the patient. In this manner, there would be many more candidates among critically ill patients who could withstand such a surgical procedure, without adversely affecting the health of the patient. Also, since such a device does not come into contact with the blood, the possibility of damaging the blood, is avoided, or at least the chance thereof, is greatly reduced.

DISCLOSURE OF INVENTION

Therefore, the principal object of the present invention is to provide a new and improved implantable heart assist device, and a method of implanting it, whereby the heart assist device can be quickly and conveniently implanted totally within the body of the patient and yet not come into direct contact with the blood being pumped.

Briefly, the above and further objects of the present invention are realized by providing an implantable heart assist device, and a novel method of implanting it totally within the body of a person.

The implantable heart assist device includes an elongated assembly extending transversely between the ribs of a person from the rib cage to the aorta of the heart to be assisted. The elongated means includes an aorta compressing means at the front end thereof for engaging the aorta externally thereof. Mounting means at the rear end of the elongated assembly supports the device from the ribs of the person, and a motive device actuates and de-activates the compressing means alternatingly to help pump blood through the aorta.

To implant the device, a small incision is made at an area between the ribs, and the device is inserted through the incisional opening, between a pair of ribs, until the aorta compressing means engages the aorta. Thereafter, the mounting means are affixed to the rib cage, and the motive means activates the aorta compressing means.

In this manner, excessive trauma to the patient is greatly reduced, and the implantation procedure can be accomplished in an extremely short period of time as compared to prior known techniques. Thus, there are many more candidates, many of whom may be critically ill, for such a device and procedure.

Moreover, the motive means may be completely electrical in nature, and thus no air tubes are required. Also, the patient need not be tethered to a large, bulky base unit.

A portion of the device is disposed in a skin pack, so that access can be readily gained thereto, without the need for complex surgery. Thus, a battery pack, and electronic control circuits of the motive means can be replaced, or the battery recharged in a convenient manner, since these items are located outside of the rib cage.

BRIEF DESCRIPTION OF DRAWINGS

The above-mentioned and other objects and features of this invention and the manner of attaining them will become apparent, and the invention itself will be best understood by reference to the following description of embodiments of the invention taken in conjunction with the accompanying drawings, wherein.

BEST MODE FOR CARRYING OUT THE INVENTION

Figure 1:
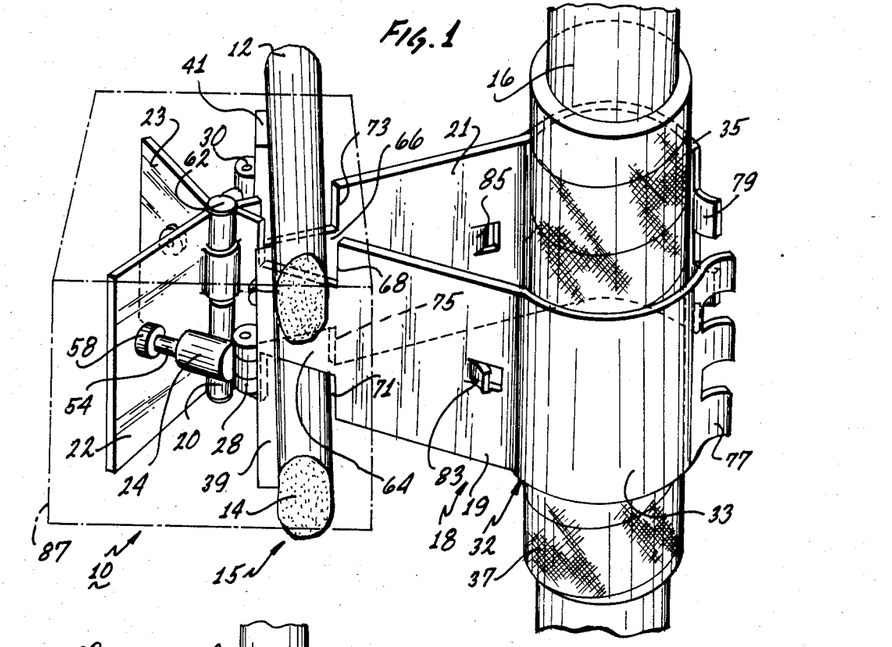
FIG. 1 is a pictorial fragmentary view of an implantable heart assist device extending between the patient's aorta and the patient's ribs (shown fragmentarily), which device is constructed in accordance with the present invention, and which is shown with the housing therefor illustrated in phantom lines, and a protective boot therefor being omitted for illustration purposes.

Referring now to the drawings, and more particularly to FIG. 1 thereof, there is shown a heart assist device 10, which is constructed in accordance with the present invention, and which is shown implanted within a human body of a patient. The device 10 is mounted between a pair of ribs 12 and 14 of a rib cage generally indicated at 15, of the body of the patient for alternately squeezing and releasing an aorta 16 of a human heart (not shown) to help increase blood flow by counterpulsation.

Counterpulsation of the blood flow means that the alternate compressing and releasing of the aorta is accomplished in synchronism with the heart beat such that the compression occurs during diastole and the release occurs during systole. Thus, during diastole, the heart is at rest and blood pressure is low. The aorta is squeezed to propel blood both distally away from the heart to improve circulation, and toward the heart, and thus into the coronary arteries (not shown) to help nourish and strengthen the heart muscle.

Since the device 10 is operative only during the low pressure cycle of the heart function, there are smaller energy demands for the device 10, as compared to conventional left ventricle assist devices, which function during the high pressure cycle of the heart. Thus, the device 10 does not require large, bulky power sources, and is totally implantable.

The heart assist device 10 generally comprises an elongated assembly 18, which is in the form of a pair of tongs. The assembly 18 includes a pair of elongated blades or arms 19 and 21, which are hingedly connected together by a vertical, separable hinge 20 disposed outside of the rib cage 15, to pivot about the hinge 20 reciprocatively. A pair of rear end portions 22 and 23 of the assembly 18 are moved by a pair of small piston cylinder assemblies 24 and 26, which are pivotally attached at their rear ends to the outer surface of the ribs 12 and 14 at the respective pivotal attachments 28 and 30.

An aorta compressor 32 includes a pair of forward curved gripping devices 33 and 35 at the distal ends of the respective arms 19 and 21, for engaging diametrically opposed portions of a reinforcing protective bandage 37 wrapped about the outer circumference of a portion of the aorta 16.

Figure 2:
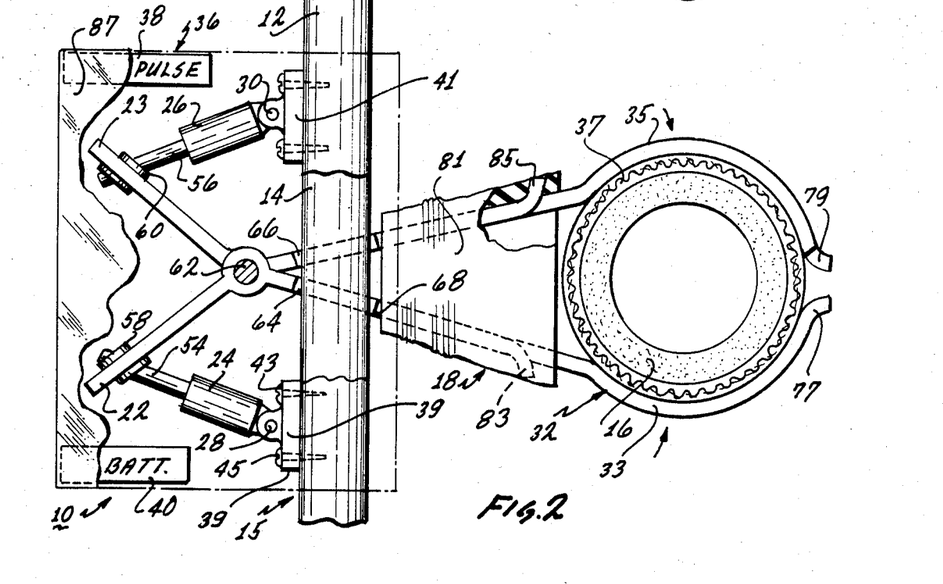
FIG. 2 is a plan view of the heart assist device of FIG. 1, the device being shown partially broken away for illustration purposes, and the patient's rib structure being shown broken away for illustration purposes.

As shown in FIG. 2, an aorta compressing motive device, generally indicated at 36, includes a pulse source 38, energized by a source of electrical power, in the form of a battery pack 40, to activate and de-activate the assemblies 24 and 25 alternatingly. The electrical connections for the source 38 and the pack 40 are not shown for illustration purposes. As a result, the gripping devices 33 and 35 alternatingly squeeze and release the aorta 16 to produce counterpulsation.

Considering now the heart assist device in greater detail with particular reference to FIGS. 1 and 2 of the drawings, a pair of upright, spaced-apart mounting or base plates 39 and 41 extend vertically between the ribs 12 and 14 to support the device 10 therefrom. A pair of mounting screws 43 and 45 fasten the upper portion of the plate 39 to the upper rib 12. A pair of similar screws (not shown) fasten the lower portion of the plate 39 to the lower rib 14.

It should be understood that the device 10 is positioned between the ribs 12 and 14 opposite the aorta 16. In order to accomplish this, using a posterior approach, an incision is made in the patient, and the device 10 is inserted therein to extend forwardly within the rib cage 15 to engage the descending portion of the aorta 16. Alternatively, as hereinafter described in greater detail, using an anterior approach, an incision can be made in the patient, and the device 10 is then positioned therein to extend to the ascending portion of the aorta 16.

In either approach, the portion of the device 10 disposed outside of the rib cage 15 is contained within a skin pack (not shown), which is a bulge or cavity covered by the patient's skin, in a similar manner to a skin pack used to cover over a conventional pacemaker.

The piston cylinder assemblies 24 and 26 include a pair of piston rods 54 and 56, which are connected to the respective rear end portions 22 and 23 at a pair of respective flexible rubber grommets 58 and 60. A hinge pin 62 secures the hinge 20 in a vertical position as shown in the drawings, and is adapted to be removed during implantation of the device 10 to separate the arms 19 and 21 for facilitating the insertion of them between the ribs 12 and 14.

A pair of narrowed portions 64 and 66 of the respective arms 19 and 21 are disposed in the space between the ribs 12 and 14 of the rib cage 15. The narrowed portion 64 is defined by a pair of upper and lower cutouts or notches 68 and 71. Similarly, the narrowed portion 66 is defined by a pair of upper and lower cutouts or notches 73 and 75. In this manner, during implantation, the separated arms 19 and 21 are each inserted sequentially between the ribs and moved in a horizontal plane, until the aorta 16 is engaged by the front end thereof. Thereafter, the arms are each rotated about their longitudinal axes, until they are disposed in a vertical plane as shown in FIG. 1.

In this manner, the large aorta compressing gripping devices 33 and 35 are greater in height than the distance between the ribs 12 and 14, and yet the gripping devices can be slipped between the ribs by turning the arms on their sides, according to the foregoing description. The notches enable the arms to be positioned upright with their longitudinal axes disposed in vertical planes, since the notches are disposed between the ribs, as shown in the drawings, when the arms are disposed in their implanted positions. Once the arms are disposed in their final positions, the hinge pin 62 can then be inserted into the hinge to retain the arms pivotally, together as shown in the drawings.

The distal end portions of the curved gripping devices 33 and 35 employ interleaved fingers 77 and 79, respectively so that when the gripping devices close about the aorta 16 to squeeze it, the ends of the gripping devices are interleaved. In order to render the device 10 relatively fail safe, the lengths of the piston rods 54 and 56 are suitably dimensioned to prevent the gripping devices from occluding the aorta completely. Instead, when the piston rods 54 and 56 are fully retracted, the gripping devices 33 and 35 are fully closed about the aorta 16 for compression purposes, but the aorta is not entirely closed off. Thus, should the device 10 inadvertently malfunction in that mode, restricted blood flow could continue until the malfunction is corrected, thereby protecting the patient from an inadvertent life-threatening termination of blood flow.

In order to prevent fibrous ingrowth into the device 10 disposed within the rib cage 15, a tubular resilient boot protector 81 surrounds the arms 19 and 21 between the ribs and the aorta. The boot protector 81 is composed of suitable resilient and stretchable material, for enabling the protector 81 to be tightly wrapped about the arms after they are disposed in their final position. A pair of struck-out boot retainer ears 83 and 85 extending outwardly from the sides of the respective arms 19 and 21, help secure the protector 81 in place.

A housing 87, shown in phantom lines, is disposed about the rear portion of the heart assist device 10 and is disposed substantially outside of the rib cage 15 within the skin pack (not shown).

METHOD OF IMPLANTATION

In order to implant the device 10 in a fast and efficient manner, a thoracotomy is performed, either employing an anterior or a posterior approach. In both procedures, an incision is made between adjacent ribs. Thereafter, by working through the incisional opening, the bandage 37, which is composed of a suitable material, is wrapped about the portion of the aorta 16, in the position as shown in the drawings, by using suitable conventional instruments (not shown).

One of the arms of the device 10 is positioned with its aorta gripping device disposed opposite the incisional opening, and is then inserted manually through the incisional opening, until the gripping device engages the bandaged portion of the aorta 16, in the manner as described previously. The other arm is then inserted through the opening into the body, in a similar manner. It should be understood that as the arms are being inserted into the body, the boot protector 81 is held in place and the arms are slipped therethrough. The hinge pin 62 is then inserted into the hinge 20 to assemble the device.

The mounting or base plates 39 and 41 of the device 10 are then fastened to the ribs 12 and 14. The device 10 can then be set into operation. The pulse source 38 is triggered by an R sensor (not shown), and, in turn, controls the piston cylinder assemblies 24 and 26 for reciprocating the arms 19 and 21.

The housing is then placed over the aorta compressing motive device 36 on the outside of the rib cage. The incisional opening is then closed in a conventional manner, to cover over the housing with the patient's skin, to form a skin pack or bulge.

ALTERNATIVE DEVICE

Figures 3, 4:
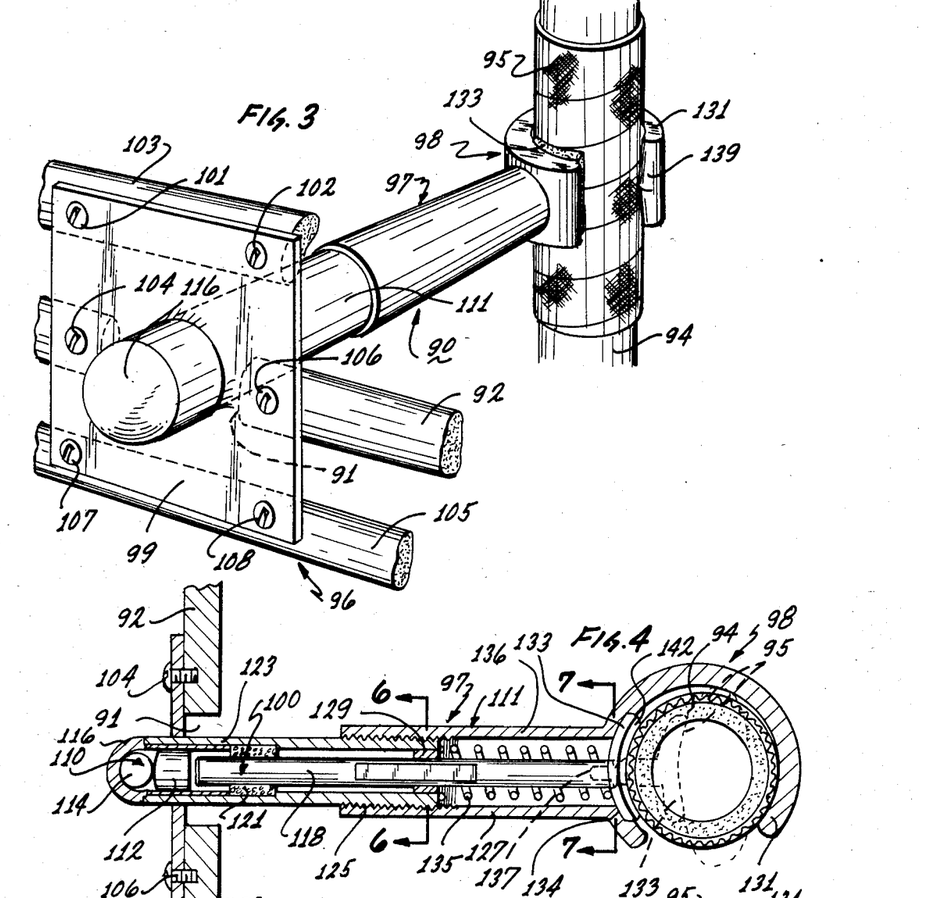
FIG. 3 is a pictorial, fragmentary view of another implantable heart assist device extending between the patient's aorta and the patient's ribs (shown fragmentarily), which device is constructed in accordance with the present invention.
FIG. 4 is a sectional plan view of the heart assist device of FIG. 3.
Figure 7:
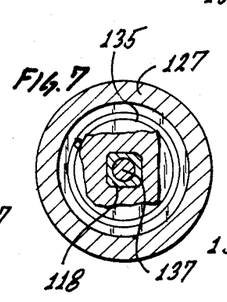
FIG. 7 is a sectional view of FIG. 4 taken substantially on line 7—7.

Referring now to FIGS. 3, 4, and 7, there is shown a heart assist device 90, which is also constructed in accordance with the present invention. The device 90 extends within an opening 91 in a resected rib 92 to an aorta 94 wrapped in a protective bandage 95. The device 90 functions in a similar manner as the device 10, and is surgically implanted according to a similar method.

The device 90 generally comprises an elongated tubular member 97 having a mounting plate 99 fixed to the rear end portion thereof and adapted to be fastened to the rib cage generally indicated at 96. An aorta gripping device 98 is disposed at the front end of the elongated member 97 to partially surround the bandaged portion of the aorta 94.

As shown in FIG. 4, a piston cylinder assembly 100 is disposed within the elongated tubular member 97 for actuating the gripping device 98 reciprocatively to produce counterpulsation action, in the same manner as the device 10 of FIG. 1. In order to support the device 90 from the rib cage 96, a pair of screws 101 and 102 extend through the plate 99 into an upper rib 103. A pair of screws 104 and 106 extend through the mounting plate 99 into the resected rib 92 on opposite sides of the opening 91. Similarly, a pair of screws 107 and 108 extend through the mounting plate 99 into a lower rib 105.

As shown in FIG. 4, an aorta compressing motive device 110 is mounted within the rear end portion of a tubular telescoping housing 111, for energizing reciprocatively the piston cylinder assembly 100. The motive device 110 includes a pulse source 112 and a power source in the form of a battery pack 114 for energizing repeatedly, the piston cylinder assembly 100, in the same manner as the pulse source 38 and the battery pack 40 of FIG. 2 energize selectively the piston cylinder assemblies 24 and 26. The electrical interconnections for the pulse source 112 and the battery pack 114 are omitted for illustration purposes.

A hemispherically shaped access door 116 is disposed at the distal rear end of the telescoping tubular housing 111 outside of the rib cage 96, to permit access to the motive device 110, as well as to the piston cylinder assembly 100. The portion of the device 60 extending outside of the rib cage is covered over by a skin pack (not shown), in a similar manner as the device 10.

Considering now the piston cylinder assembly 100 in greater detail, the assembly 100 includes a piston rod 118 surrounded at its rear end portion by an integral solenoid field 121 positioned within an inner tubular member 123 of the telescoping housing 111. The housing 111 includes a forwardly disposed outer tubular member 127 threadably attached at 125 to the rearwardly disposed inner tubular member 123. A keyed bushing 129 supports the piston rod 118 within the forward end of the inner member 123.

The gripping device 98 generally comprises a circular hook-shaped member 131 which is integrally connected to the forward end of the outer telescoping tubular member 127 for attaching conveniently to the bandaged portion of the aorta 94. A smoothly contoured or curved pusher plate 133 is fixed to the forward end of the piston rod 118 and is positioned within a recess 134 within the hook-shaped member 131, to move reciprocatively for squeezing and releasing alternatively the bandaged portion of the aorta 94, as indicated by the broken lines illustrated in FIG. 4. A return spring 135 surrounds the piston rod 118 within the outer telescoping member 127, to cause the piston cylinder assembly 100 to de-activate. In order to connect the pusher plate 133 to the piston rod 118, a pusher plate shank 136 is threaded into a tapped opening in the forward distal end of the piston rod 118.

Figure 5:
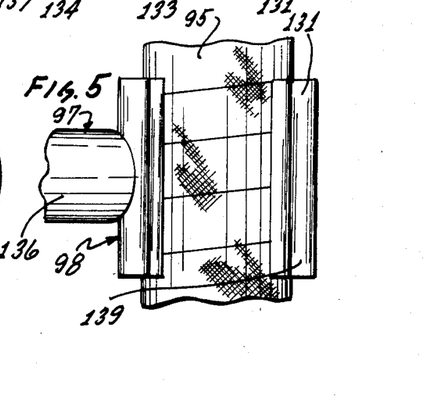
FIG. 5 is a side-elevational view of the aorta gripping portion of the device of FIG. 4.
Figure 6:
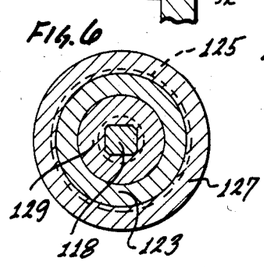
FIG. 6 is a sectional view of FIG. 4 taken substantially on line 6—6 thereof.

For the purpose of deforming the bandaged aorta 94 in a smooth, progressive manner to avoid stressing it unduly, the hook-shaped member 131 has an inner smoothly contoured surface 139 (FIG. 5) having a thicker central portion tapered gradually outwardly therefrom. As shown in FIG. 4, the pusher plate 133 has a similarly contoured surface 142 to compress the bandaged aorta 94 between the pusher plate 142 and the inner contoured surface 139 of the hook-shaped member 131.

The method of implantation of the device is very similar to the method of implantation of the device 10. The only difference between the two implantation procedures is that the rib 92 is resected by removing a portion thereof, to create the opening 91 in the rib cage 96 to enable the device 90 to extend into the body so that the aorta gripping device 98 partially encircles the bandaged portion of the aorta 94. Once in position, the mounting plate 99 is fastened to the rib cage 96 as mentioned previously.

Figures 8, 9:
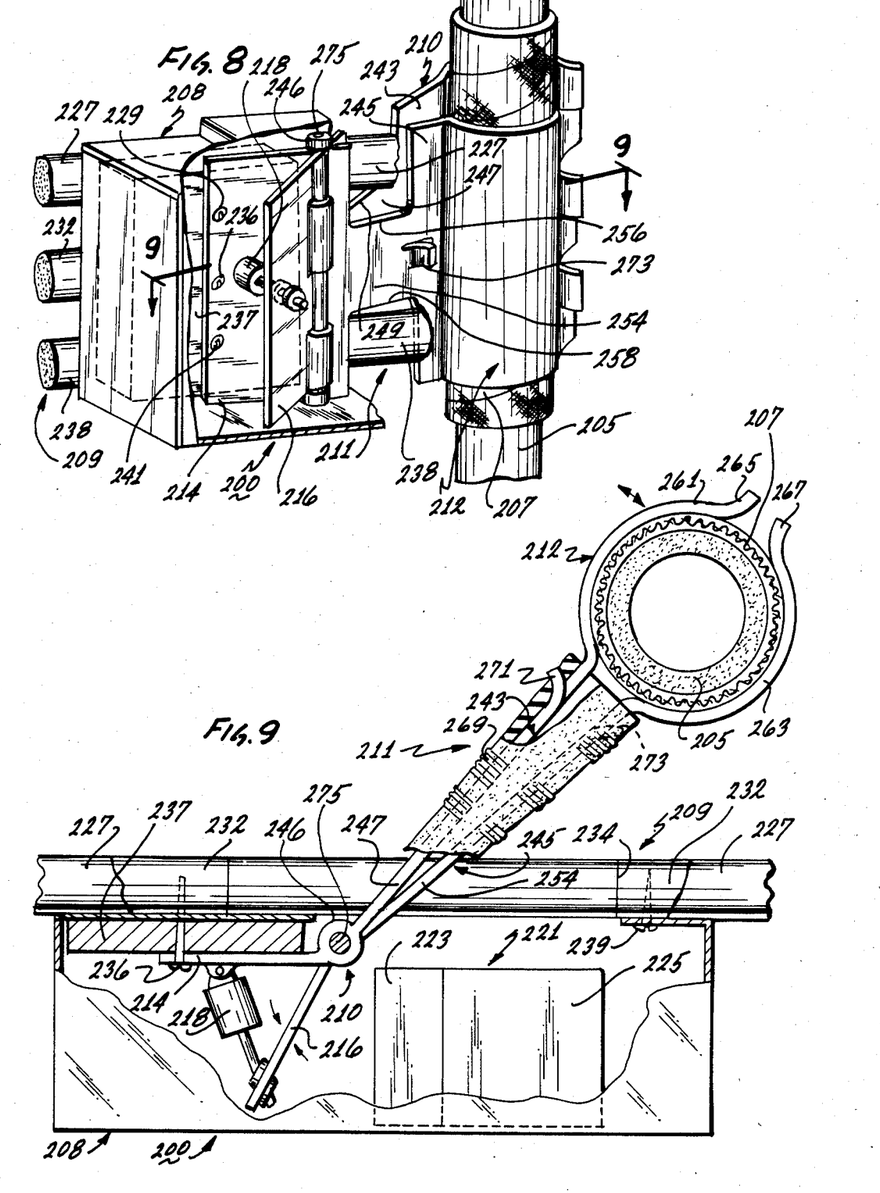
FIG. 8 is a fragmentary, pictorial view of an implantable heart assist device extending between the patient's aorta and the patient's ribs (shown fragmentarily), which device is constructed in accordance with the present invention, and which is shown with the protected boot therefor being omitted for illustration purposes.
FIG. 9 is a sectional plan view of the heart assist device of FIG. 8, the device and the patient's rib structure being shown broken away for illustration purposes.

Referring now to the drawings, and more particularly to FIGS. 8 and 9 thereof, there is shown a heart assist device 200, which is constructed in accordance with the present invention, and which is shown implanted within a human body of a patient. The device 200 is adapted to squeeze and release alternately an aorta 205 of the patient to help increase the blood flow rate of the human heart (not shown), according to counterpulsation techniques.

Counterpulsation of the blood flow means that the alternate compressing and releasing of the aorta is accomplished in synchronism with the heart beat such that the compression occurs during diastole and release occurs during systole. Thus, during diastole, the heart is at rest and blood pressure is low. The aorta is squeezed to propel blood both distally away from the heart to improve circulation, and toward the heart, and thus into the coronary arteries (not shown) to help nourish and strenghten the heart muscle.

Since the device 200 is operative only during the low pressure cycle of the heart function, there are smaller energy demands for the device 200, as compared to conventional left ventricular assist devices, which function during the high pressure cycle of the heart. Thus, the device 200 does not require large, bulky power sources, and is totally implantable.

A suitable reinforcing bandange 207 is wrapped about the aorta 205 to protect it during the squeezing and releasing operation of the device 200. In this manner, the forces exerted on the aorta are spread uniformly over the area of compression.

The heart assist device 200 generally comprises a housing 208, which is attached to the rib cage 209 on the outside thereof, for supporting the device 200 therefrom. In this manner, the housing 208 can be conveniently covered over by the skin (not shown) of the patient in a skin pack. In this manner, access can be gained readily to the working parts of the device 200, for repair or replacement thereof.

The device 200 includes an elongated assembly 211, which includes tongs 210 having an aorta gripping device 212 positioned about the bandaged portion of the aorta 205. The tongs 210 include a fixed handle portion 214 secured to the rib cage 209, and a movable handle portion 216 which is moved reciprocatively relative to the portion 214 by means of a piston cylinder assembly 218. By employing a fixed handle portion 214, only a single piston cylinder assembly need be employed.

As shown in FIG. 9, an aorta compressing motive device, generally indicated at 221, includes a pulse source 223, energized by a source of electrical power, in the form of a battery pack 225. The entire motive device 221 is disposed within the housing 208 behind an access door (not shown).

In order to fix the device 200 to the rib cage 209, a screw 229 fixes the upper portion of the device 200 to an upper rib 227. An intermediate resected rib 232 has a removed portion (not shown) leaving an opening 234 (FIG. 2), through which extends the elongated assembly 211. The device 200 is also fixed to the rib cage 209 by means of a screw 236, which extends through the handle portion 214, a spacer block 237, the housing 208 and into the rib 232. As shown in FIG. 9, a similar screw 239 fastens the other end of the housing 208 to the rib 232 at the opposite end of the opening 234.

A screw 241 fastens the housing 208 to a lower rib 238. Additionally, other mounting screws are also provided, but they are not illustrated in the drawings for sake of clarity.

The tongs 210 include a pair of elongated blades or arms 243 and 245, which are hingedly connected together by a vertical, separable hinge 246, disposed outside of the rib cage 209, to pivot about the hinge 246 reciprocatively. The arm 243 includes a narrow web portion 247 defined by an upper notch 249 and a similar lower notch (not shown). Similarly, the arm 235 includes a narrow web portion 254 defined by an upper notch 256 and a lower notch 258. In this manner, the narrow web portions 247 and 254 extend between the upper and lower ribs 227 and 238, respectively.

The gripping device 212 includes a pair of curved portions 261 and 263 for receiving the bandaged portion of the aorta 205. The curved portions 261 and 263 include respective spaced-apart fingers 265 and 267, which are adapted to be interleaved when the gripping device 212 squeezes the aorta 205 tending to flatten it.

As shown in FIG. 9, a protective boot 269 surrounds the arms 263 and 265 between the rib cage and the aorta to prevent fibrous ingrowth. A pair of ears 271 and 273 on the respective arms 243 and 245 secure the boot 279 in place thereon. The boot 269 is composed of suitable stretchable resilient material.

METHOD OF IMPLANTATION

In order to implant the device 200 in a fast and efficient manner, a thoracotomy is performed, either employing an anterior or a posterior approach. With both procedures, an incision is made between adjacent ribs. Thereafter, by working through the incisional opening, the intermediate rib 232 is resected by removing a portion thereof to provide the opening 234 to facilitate the insertion of the device 200.

By working through the opening 234, the bandage 207 is wrapped about the portion of the aorta 205 opposite the opening 234. Suitable conventional instruments (not shown) may be used for this procedure.

One of the arms of the device 200 is positioned with its aorta gripping device disposed opposite the incisional opening, and is then inserted manually through the incisional opening, until the gripping device engages the portion of the aorta 205, in the manner as described previously. The other arm is then inserted through the opening into the body, in a similar manner. It should be understood that when the arms are inserted into the body, the protective boot 269 is held in place, and the arms are slid therethrough during the procedure. The hinge pin 275 of the hinge 246 is then inserted thereinto for the purpose of completing the assembly of the device 200. The screws are then inserted in place into the respective ribs to fix the device in place. In this regard, the device 200 is completely supported by the rib cage 209 by means of the screws, which attach the housing 208 in place.

The device 200 can then be set into operation. The pulse source 223 is triggered by a conventional R sensor (not shown), and the source 223 in turn, controls the piston cylinder assembly 218 for reciprocating the arm 245 relative to the fixed arm 243.

The incisional opening is then closed in a conventional manner to cover over the housing with the patient's skin, to form a skin pack or bulge.

Figure 10:
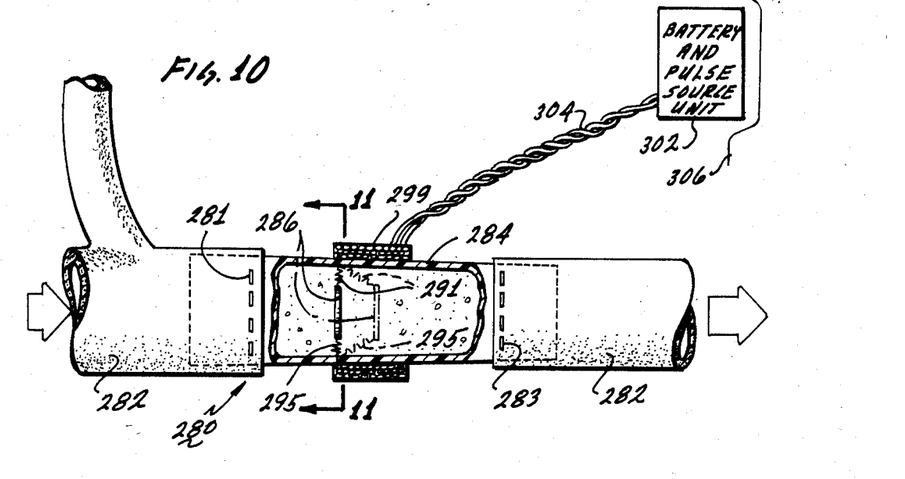
FIG. 10 is a fragmentary side elevational view of another implantable heart assist device connected in-line with a patient's aorta, which device is constructed in accordance with the present invention.
Figures 11, 12:
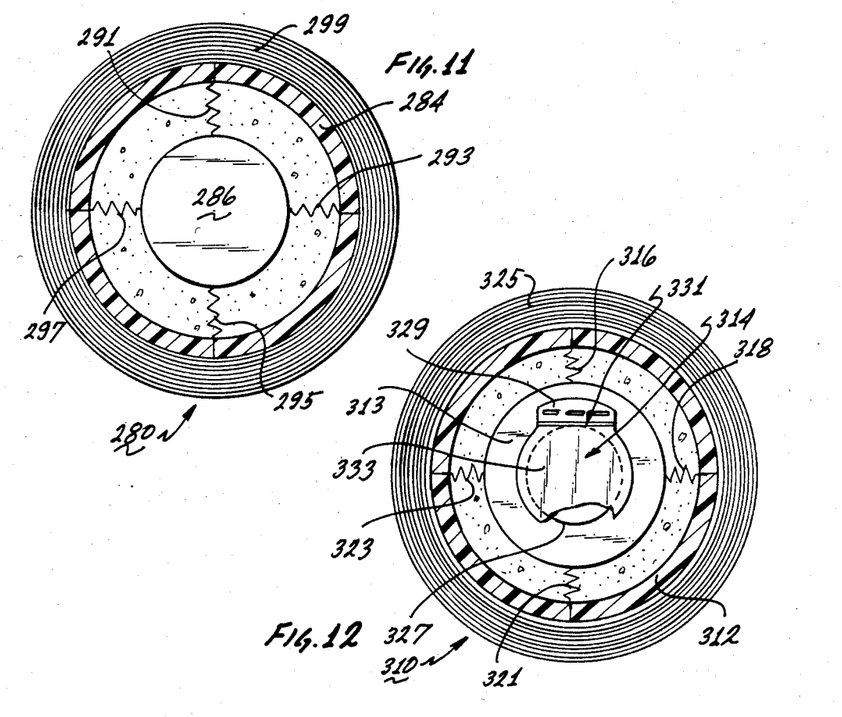
FIG. 11 is an enlarged sectional view of the device of FIG. 3 taken substantially on line 11—11 thereof.
FIG. 12 is a sectional plan view, similar to FIG. 11, of a further heart assist device connected in-line with a patient's aorta, which device is also constructed in accordance with the present invention.

Referring now to FIGS. 10 and 11 of the drawings, there is shown another heart assist device 280, which is constructed in accordance with the present invention. The device is connected in fluid communication with a resected portion of an aorta 282, by any suitable means, such as the sutures 281 and 283. In this manner, the device 280 is attached sealingly in line with the resected aorta.

The device 280 is particularly well suited for use with an aorta which is unable to withstand being squeezed repeatedly, such as the device 200 of FIGS. 8 and 9.

The device 280 generally comprises an elongated flexible tubular conduit 284, which includes a metallic valve member 286 disposed within the conduit 284. A series of four springs 291, 293, 295, and 297 extend radially from the circular valve member 286 to position it transversely relative to the central axis of the conduit 284.

An annular electrical winding 299 surrounds the central portion of the conduit 284 and, when energized by a battery and pulse source unit 302, creates a magnetic field with the tubular conduit 284 for attracting the metallic valve member 286 to cause it to move forwardly into the position as illustrated in broken lines in FIG. 11. When the unit 302 interrupts the electric current to the winding 299 for terminating the magnetic field, the springs cause the valve member 286 to snap abruptly rearwardly into the solid line position as shown in FIG. 11. In this manner, the valve member 286 helps propel the blood through the aorta 282 in the direction of the large arrows as the valve member 286 is moved back and forth repeatedly in synchronism with the heart beat.

Lead wires 304 extend from the annular winding 299 to the battery and pulse source unit 302. The unit 302 is covered over by a skin pack schematically shown at 306 in a similar manner as the device 200 of FIG. 8.

The inside diameter of the conduit 284 is tapered slightly convergingly in a downstream direction. In this manner, as the valve member 286 is attracted forwardly in a downstream direction, the tranversely disposed valve member 286 occupies a progressively greater portion of the cross-sectional area of the conduit 284. In this manner, as the valve member 286 moves forwardly, it is increasingly more effective in displacing the blood disposed within the conduit 284.

However, for safety reasons, the valve member 286 does not cut-off the blood flow in its extreme forward position illustrated in broken lines in FIG. 10. In this regard, should the winding 299 inadvertently malfunction, the valve member 286 could not completely cut-off the blood flow.

The implantation procedure includes severing the aorta 282, and then inserting the ends of the conduit 284 into the severed ends of the aorta 282. The aorta 282 is then attached to the conduit 284 by suturing the ends of the tubular conduit 284 to the aorta 282 by the sutures 281 and 283. The unit 302 is mounted externally of the rib cage (not shown) beneath the skin pack 306. The unit 302 energizes the winding 299 via the wire leads 304.

Referring now to FIG. 12, there is shown another heart assist device 310, which is constructed in accordance with the present invention, and which is similar to the device 280. The device 310 is connected sealingly in line with a resected aorta (not shown).

The device 310 includes an elongated tubular conduit 312, having a valve member 313 mounted tranversely therein, in a similar manner as the valve member 286 as mounted in the conduit 284.

The conduit 312 is generally circular in cross-section throughout its length, is composed of suitable flexible material, and is similar to the conduit 284.

A check valve flap 314 is disposed over the downstream side of a centrally-disposed circular opening 327 in the valve member 313. The flap 314 serves as a check valve to facilitate the retraction of the valve member 313.

In this regard, a series of four springs 316, 318, 321, and 323 extend radially between the valve member 314 and the tubular conduit 312. An annular electrical winding 325 surrounds the exterior of the conduit 312, to move the metallic valve member 313 down-stream within the conduit 312, in a similar manner as the winding 299 moves the metallic valve member 286 of the device 280.

In order to secure the flap 314 to the valve member 313, a tab 329 is connected through a living hinge 331 to the body portion 333 of the flap 314. The tab 329 is suitably secured to the valve member 313, by any suitable technique.

While particular embodiments of the present invention have been disclosed, it is to be understood that various different modifications are possible and are contemplated within the true spirit and scope of the appended claims. For example, different suitable materials may be employed for the various components of the devices shown and described herein. There is no intention, therefore, of limitations to the extact abstract or disclosure herein presented.

We claim:

1. An implantable device for assisting the functioning of the heart of a person, comprising:
   an elongated assembly for extending transversely between the ribs of the person from the ribs to the aorta of the heart to be assisted, said assembly including means for engaging externally and compressing the aorta at the front end thereof;
   motive means for actuating and de-activating said compressing means cyclically to help pump blood through the aorta; and
   housing means for said elongated assembly said housing including mounting means for supporting said device from the ribs of the person, said housing having a distal end portion for projection outside of the rib cage for permitting access to the interior of said assembly while in place within the body.

2. An implantable device according to claim 1, wherein said mounting means comprises:
   fastening means for fastening said device to an outer surface of the ribs.

3. An implantable device according to claim 2, wherein said mounting means includes a pair of spaced-apart plates adapted to extend between the ribs and to be fastened thereto.

4. An implantable device according to claim 1, wherein said assembly includes a housing for confining said motive means, and said housing is disposed rearwardly of said mounting means for positioning it outwardly of the ribs.

5. An implantable device according to claim 4, wherein said motive means includes electrical pulse producing means for controlling the repetitions of said compressing means, and a source of electrical energy activates said pulse producing means.

6. An implantable device according to claim 5, wherein said aorta compressing means includes a pair of first and second spaced-apart gripping means for receiving a portion of the aorta therebetween, and said motive means causes relative movement of said gripping means toward and away from one another to compress and release repeatedly the portion of the aorta disposed therebetween.

7. An implantable device according to claim 5, wherein said aorta compressing means includes a pair of first and second elongated arms pivotally attached together, and said first and second members having respective first and second oppositely-disposed, spaced apart aorta gripping means at the front end portions thereof for receiving a portion of the aorta therebetween.

8. An implantable device according to claim 7, wherein said motive means includes means for moving the rear end portions of said elongated arms toward and away from one another to cause relative movement of said first and second aorta engaging devices toward and away from one another.

9. An implantable device according to claim 7, wherein one of said rear end portions is secured to the ribs of the person.

10. An implantable device according to claim 7, wherein said motive means includes a piston cylinder assembly.

11. An implantable device according to claim 7, wherein said aorta compressing means includes hook-shaped means for partially encircling the aorta, and plunger means for squeezing the aorta between said plunger means and said hook-shaped means.

12. An implantable device according to claim 11, wherein said elongated assembly includes tubular telescoping members, and said motive means is disposed within said members.

13. An implantable device according to claim 12, wherein said motive means includes a piston cylinder assembly for activating said plunger means.

14. A method with reduced surgical trauma of implanting in a patient a heart assist device having an aorta compressing means, comprising:
   making an incision in the patient between adjacent ribs of the rib cage of the patient opposite a portion of the aorta;
   inserting the device into the incisional opening between the ribs until the aorta compressing means engages the aorta; and
   attaching the device to the ribs.

15. A method according to claim 14, wherein the device is elongated in shape and has motive means outside of the rib cage, and closing said incisional opening to cover over said motive means with skin of the patient.

16. A method according to claim 14, further including resecting a portion of at least one of said ribs to help form the opening.

* * * * *